US012623000B2

(12) United States Patent

Yoo et al.

(10) Patent No.: US 12,623,000 B2

(45) Date of Patent: May 12, 2026

(54) COMPOSITION FOR TRANSPLANTATION OF ORGANOID

(71) Applicant: ORGANOIDSCIENCES, LTD., Seongnam-si (KR)

(72) Inventors: Jong Man Yoo, Seongnam-si (KR); Joo Hyun Jee, Seongnam-si (KR); Sang Yun Jung, Seongnam-si (KR); Han Kyung Kim, Seongnam-si (KR); Joong Woon Lee, Seongnam-si (KR)

(73) Assignee: ORGANOIDSCIENCES, LTD., Seongnam-si (KR)

( * ) Notice: Subject to any disclaimer, the term of this patent is extended or adjusted under 35 U.S.C. 154(b) by 1113 days.

(21) Appl. No.: 17/298,833

(22) PCT Filed: Oct. 15, 2019

(86) PCT No.: PCT/KR2019/013527

§ 371 (c)(1),
(2) Date: Mar. 28, 2022

(87) PCT Pub. No.: WO2020/111507

PCT Pub. Date: Jun. 4, 2020

(65) Prior Publication Data

US 2022/0226538 A1 Jul. 21, 2022

(30) Foreign Application Priority Data

Nov. 30, 2018 (KR) ........................ 10-2018-0152804

(51) Int. Cl.
*A61L 27/22* (2006.01)
*A61L 27/24* (2006.01)
(Continued)

(52) U.S. Cl.
CPC ........... *A61L 27/222* (2013.01); *A61L 27/225* (2013.01); *A61L 27/24* (2013.01); *A61L 27/26* (2013.01);
(Continued)

(58) Field of Classification Search
CPC ...... A61L 27/222; A61L 27/225; A61L 27/24; A61L 27/26; A61L 27/3804; A61L 2400/06
See application file for complete search history.

(56) References Cited

U.S. PATENT DOCUMENTS

2011/0224675 A1* 9/2011 Tofighi ............... A61B 17/8811
606/92
2012/0196312 A1* 8/2012 Sato ..................... C12N 5/0677
435/405

(Continued)

FOREIGN PATENT DOCUMENTS

JP 2018-531011 A 10/2018
KR 10-2014-0037210 A 3/2014
(Continued)

OTHER PUBLICATIONS

Joohyun Jee et al., "In vivo evaluation of scaffolds compatible for colonoid engraftments onto injured mouse colon epithelium", The FASEB Journal, Sep. 2019, pp. 10116-10125, vol. 33, Issue 9.
(Continued)

*Primary Examiner* — Jianfeng Song

(74) *Attorney, Agent, or Firm* — Sughrue Mion, PLLC

(57) ABSTRACT

The present invention relates to a composition for transplantation comprising an organoid, and a use of same. According to one example, using collagen, gelatin or fibrin glue as a scaffold for organoid transplantation results in a high transplantation rate and a high survival rate of organoid as well as desirable stability.

3 Claims, 10 Drawing Sheets

(51) Int. Cl.
    *A61L 27/26*        (2006.01)
    *A61L 27/38*        (2006.01)

(52) U.S. Cl.
    CPC ....... *A61L 27/3804* (2013.01); *A61L 2400/06*
                                 (2013.01)

(56)                References Cited

U.S. PATENT DOCUMENTS

2014/0243227 A1 *   8/2014   Clevers .................. C12N 5/067
                                                     506/10
2017/0292116 A1    10/2017   Wells et al.

FOREIGN PATENT DOCUMENTS

| | | |
|---|---|---|
| KR | 10-2018-0038573 A | 4/2018 |
| WO | 2012/168930 A2 | 12/2012 |
| WO | 2017/149025 A1 | 9/2017 |

OTHER PUBLICATIONS

Notification of Reason for Refusal of Korean Application No. 10-2018-0152804 dated May 22, 2020.
Notice of Final Rejection of Korean Application No. 10-2018-0152804 dated Dec. 30, 2020.
Notice of Final Rejection of Korean Application No. 10-2018-0152804 dated Apr. 2, 2021.
International Search Report of PCT/KR2019/013527 dated Jan. 17, 2020 [PCT/ISA/210].
Written Opinion of PCT/KR2019/013527 dated Jan. 17, 2020 [PCT/ISA/237].

* cited by examiner

COMPOSITION FOR TRANSPLANTATION OF ORGANOID

CROSS REFERENCE TO RELATED APPLICATIONS

This application is a National Stage of International Application No. PCT/KR2019/013527, filed Oct. 15, 2019, claiming priority to Korean Patent Application No. 10-2018-0152804, filed Nov. 30, 2018, the entire disclosures of which are incorporated herein by reference.

TECHNICAL FIELD

The present invention relates to a composition for transplantation of an organoid, and a use of same.

BACKGROUND ART

Organoids are considered basic experimental models, sources of implantable tissue, and physiologically relevant platforms for drug screening. In contrast to a culture of immortalized cells, intestinal organoids, for example, contain viable stem cells residing in crypt-like lobes, undergo a continuous cycle of regeneration and differentiation to produce multiple functional cell types and repeat key aspects of gut development and homeostasis.

Epithelial organoids can be formed from human colon, adenoma, and adenocarcinoma tissue and cultured from personalized medicine, patient-derived crypt or ex vivo and opened up possibilities for autologous transplantation using stem cells culture and proliferated in ex vivo. Despite a histological accuracy of the original tissues, stem cell-derived organoids from the gastrointestinal tract (GI tract) have several limitations, a main one of which is depending on Matrigel as a 3D scaffold.

Matrigel is a widely used commercial product to provide a 3D scaffold for the growth of organoids of all cell types. It is used to grow intestine, retina, kidney, liver, stomach, prostate, breast, inner ear, cardiac muscle fibers, hepatic endothelium, pancreas, fallopian tubes, and cerebral organoids. It is also used for growing organoids from a variety of species including chickens, rats and humans. However, reliance on Matrigel or similar naturally derived biopolymer matrices as scaffolds for organoid growth poses several significant limitations to the study and use of the resulting organoids. Matrigel is derived from basement membrane of ECM-rich mouse sarcoma and therefore carries a high risk of transmitting immunogens or pathogens when given to a patient, particularly problematic in the field of serious patient death and morbidity related to infection following immunosuppression and it is known to promote angiogenesis and cancer development.

In addition, the batch-to-batch variability of Matrigel can lead to inconsistent cell behavior introducing unknown and potentially confounding variables that complicate the interpretation of both basic and translational research. Moreover, although Matrigel is a crucial element of the current organoid culture model, its role in organoid formation has not been elucidated.

Therefore, there is a need for research on a scaffold for human injection which is effective enough to replace a matrigel in the field of organoids and suitable for transplantation in a body.

DESCRIPTION OF THE INVENTION

Technical Problem

One aspect of the present invention is to provide a composition for biotransplantation comprising an organoid, and a gelatin, collagen, fibrin glue, or a combination of thereof.

Another aspect of the present invention is to provide a method for organoid transplantation comprising a step of mixing gelatin, collagen, fibrin glue, or a combination thereof with an organoid and a step of administering the mixture to a subject.

Technical Solution

One aspect of the present invention provides a composition for biotransplantation comprising organoid, and a gelatin, collagen, fibrin glue, or a combination thereof.

The term "organoid" as used herein refers to a cell mass having a 3D three-dimensional structure and refers to a miniaturized and simplified version of an organ prepared through an artificial culture process that is not collected or acquired from animals. The origin of the cells constituting the organoid is not limited. Organoids can be derived from tissues, stem cells, for example, embryonic stem cells or induced pluripotent stem cells, and may be cultured in three dimensions from their self-renewal and differentiation ability. The organoid may have an environment that is allowed to interact with the surrounding environment during the cell growth process. Accordingly, the 3D organoid in the present invention almost completely mimics the organs that interact in vivo and can be an excellent model for observing the development of therapeutic agents for diseases. It can similarly reproduce the physiologically active function of the human body, and by constructing an organ analogue from the patient's tissue, disease modeling based on the patient's genetic information and drug screening through repeated tests are possible. For this function, it is required to have excellent transplantation rate, engraftment ratio, survival rate and stability when transplanted into a living body. The term "gelatin" as used herein refers to a kind of a protein obtained by decomposing and purifying natural proteins composed in animal skin, cartilage, tendon, etc.

The term "collagen" as used herein refers to a protein that is most widely distributed in the human body, and although it is a main component of connective tissues, mainly in bones and skin, it is a component distributed throughout our body, such as joints, membranes of each organ, and hair. A hard protein may also be called 'collagen'.

The term "fibrin glue" as used herein refers to a tissue adhesive composed of fibrinogen, thrombin, calcium chloride, and inhibitors of anti-fibrinolytic enzyme, and is used for hemostasis in patients with lacerations. When a tissue is wounded, it refers to a substance that forms fibrin by leaking fibrinogen together with blood components from the capillaries around the cut.

The term "fibrin glue" as used herein refers to a tissue adhesive composed of fibrinogen, thrombin, calcium chloride, and inhibitors of fibrinolytic enzyme, that is used for suturing peripheral nerves, suturing microvessels, cranial nerve surgery, orthopedic surgery such as bone adhesion, and hemostasis of patients with lacerations. When a tissue is wounded, it refers to a substance that forms fibrin by leaking fibrinogen together with blood components from the capillaries around the cut.

The gelatin, collagen, and fibrin glue all have excellent biocompatibility and stability in the body.

The term "biotransplanting" or "bio implanting", as used herein refers to a phenomenon in which a composition for biotransplantation is administered to a subject and settle at the implantation site.

For biotransplantation, it is required that the transplanted site is not affected, and to have a high survival rate and transplantation rate.

The organoid is not limited thereto as long as it is an organoid that can be implanted using gelatin, collagen, fibrin glue, or a combination thereof as a scaffold. Specifically, the organoids may be selected from a group of intestinal organoids, retinal organoids, kidney organoids, liver organoids, gastric organoids, prostate organoids, breast organoids, inner ear organoids, cardiac muscle fiber organoids, liver endothelial organoids, pancreatic organoids, fallopian tube organoids, and cerebral organoids.

Gelatin may be comprised in an amount of about 2.5 to 10% (w/v) based on the total weight of the composition. If the gelatin is more than about 10% (w/v), cytotoxicity may occur to the transplanted organoids due to the endotoxicity of the gelatin.

Collagen may be comprised in an amount of about 10 to 20% (v/v) based on the total weight of the composition.

Fibrin glue may be comprised in an amount of about 10 to 15% (v/v) based on the total weight of the composition. If the fibrin glue is more than about 15% (v/v), the composition may harden too quickly and the transplantation rate of the organoid may be reduced.

The gelatin, collagen, or fibrin glue may be used by purchasing commercially available ones, separating those existing in nature, or synthesizing them.

The composition may further comprise a material that may be conventionally included when transplanting and culturing organoids.

In the composition, the organoid, gelatin, collagen, or fibrin glue may be in a form attached to a medical device for transplantation. The medical device may be selected from the group consisting of, for example, but not limited to, stents, pins, stitches, splits, pacemakers, artificial skin, and rods.

The composition according to one embodiment of the present invention may include a pharmaceutically acceptable carrier and/or additive. For example, sterile water, physiological saline, conventional buffers (phosphoric acid, citric acid, other organic acids, etc.), stabilizers, salts, antioxidants (ascorbic acid, etc.), surfactants, suspending agents, isotonic agents, or preservatives, etc. For topical administration, organic materials such as biopolymers, inorganic materials such as hydroxyapatite, specifically collagen matrix, polylactic acid polymers or copolymers, polyethylene glycol polymers or copolymers and chemical derivatives thereof, etc. may also be combined.

Another aspect of the present invention provides a cell therapy product comprising an organoid, and a gelatin, collagen, fibrin glue, or a combination of thereof.

The term "cell therapy product" or "cell therapy agent" as used herein refers to a pharmaceutical product for treatment, diagnosis, or prevention purposes using cells and tissues prepared by isolation, culture, or particular manipulation from humans. It also refers to a pharmaceutical product used for treatment, diagnosis, or prevention purposes by restoring the function of cells or tissues through procedures such as proliferating or selecting autologous, allogeneic, or xenogeneic cells ex vivo or such as changing biological properties thereof.

According to one aspect of the invention, the cell therapy agent may be used to treat a condition in which the mucosa itself is lost, such as inflammatory bowel disease or damage to the mucous membrane.

Another aspect of the present invention provides a method for organoid transplantation comprising a step of mixing gelatin, collagen, fibrin glue, or a combination thereof with an organoid and a step of administering the mixture to a subject.

Gelatin, collagen, fibrin glue, and organoids are as described above.

The subject may be a subject that needs to be formed by transplanting an organoid.

The subject includes humans and mammals, and specifically includes humans, monkeys, mice, rats, rabbits, sheep, cattle, dogs, horses, pigs.

The terms "administering," "introducing," and "transplanting" as used herein can be used interchangeably, and may refer to a placement of a composition into a subject by a method or route that results in at least partial localization of the composition to a desired site. Administration may be by any suitable route that delivers at least a portion of a cell or cellular component of a composition according to one embodiment to a desired location in a living subject.

In the above method, administration may be administered to a lesion site requiring transplantation of an organoid. Endoscopy equipment may be used for administration, but is not limited thereto. For example, administration to the esophagus, stomach, duodenum, large intestine, or colon using an endoscope is typical, and in addition, all organs in the body through surgical operations, such as salivary glands, lacrimal glands, muscles, lungs, liver, pancreas, kidney, uterus, prostate, etc. can be administered. For example, when the mucous membrane itself is lost, such as inflammatory bowel disease or damage to the mucous membrane, it can be used to replace the damaged mucosa by transplanting organoids.

The method uses collagen, gelatin, or fibrin glue as a scaffold for organoid transplantation, thereby exhibiting transplant stability and engraftment ratiosimilar to those of conventionally used matrigel, and is also clinically applicable safely.

As mentioned above, organoids can be differentiated into organoids with adult-like characteristics even in vitro, and above all, because they utilize the patient's own adult cells, there are no technical issues such as immunogenicity, and ethical problems which can be obstacles of tissue therapy in future.

Effects

According to one aspect of the present invention, when collagen, gelatin, or fibrin glue is used as a scaffold for organoid transplantation, the transplantation rate and survival rate of organoids are high, and stability is also excellent.

EXAMPLES

Figure 1:
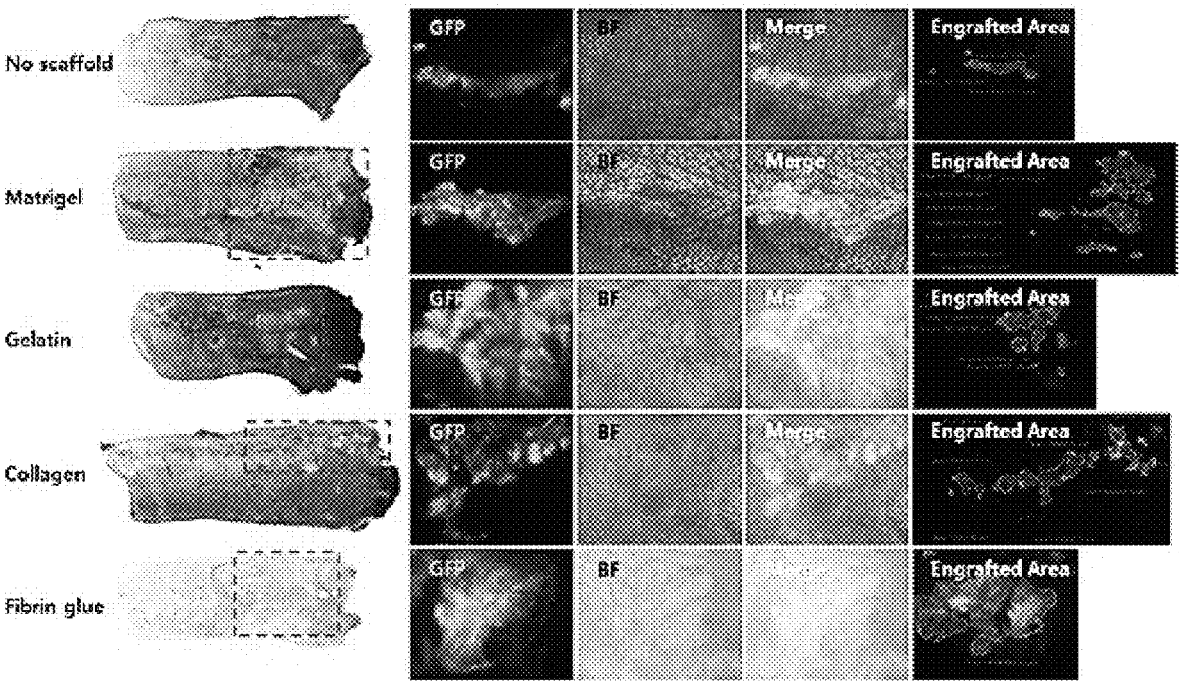
FIG. 1 is a photograph of measuring the GFP signal emitted from an organoid transplanted into the colon tissue on the 7th day after transplanting the colon organoid for each scaffold.

Hereinafter, it will be described in more detail through examples. However, these examples are for illustrative purposes of one or more embodiments, and the scope of the present invention is not limited to these examples.

Reference 1. Preparation and Culture of Colon Organoids

Colon tissue was separated from EGFP mice, and colonic crypt was isolated using an enzyme. It was inoculated into an uncoated 48-well plate wherein matrigel and medium for colon organoids were mixed in a 1:1 ratio. After checking that the matrigel was hardened 20 minutes after placed in an incubator, a medium for colon organoids was added and cultured for 5 days to prepare colon organoids for biotransplantation to be used below.

Example 1. Preparation and Transplantation of Organoids for Biotransplantation 1.1. Colon Tissue Damage Model Construction A colon tissue damage model to produce organoids was prepared as follows. Wild-type mice to be transplanted with colon organoids were exposed to 0.5M EDTA for 5 minutes, and physical damage was applied to remove the crypts of the colonic lining for 2 minutes with an electric toothbrush.

1.2. Preparation and Transplantation of Organoids for Biotransplantation

A colon organoid was prepared so that the colon organoid prepared above expresses GFP. All colon organoids were treated with 10 μM of Y-27632 in the organoid medium one day before transplantation to maximize the survival rate. In addition, the matrix used during culture was completely removed by treatment with a cell recovery solution.

Thereafter, the following three scaffolds were mixed under the conditions described below and transplanted in a volume of 50 μl into the anus of the colon tissue damage mouse model prepared in 1.1.

1) Gelatin: GFP+ colon organoids were mixed with PBS in which 5% gelatin was dissolved in a ratio of gelatin: organoid containing medium=1:2, and the resultant was transplanted. Herein, the organoid containing medium comprises 10 μM of Y-27632.

2) Collagen: GFP+ colon organoids were mixed with 100% collagen stock solution in a ratio of collagen: organoid containing medium=1:9, and the resultant was transplanted. Herein, the organoid containing medium comprises 10 μM of Y-27632.

3) Fibrin Glue: a colonoid solution was prepared by mixing GFP+ colon organoids with 45 μl of colonoid culture medium containing 10 μM of Y-27632. Fibrin was mixed with a ratio of 1:1 in a solution in which thrombin is diluted 1:100 in PBS to make 5 μl of the solution. And then, it was mixed with the prepared 45 μl of colonoid solution and the resultant was transplanted.

Matrigel was used as a control group.

Matrigel was transplanted after mixing it with a colonoid culture medium containing organoids at a concentration of 10%. At this time, the medium containing the organoids contains 10 μM of Y-27632.

After transplantation, the anus was closed using 10 μl of 3M Vetbond, and the suture was released 14 hours later to induce normal bowel activity.

Example 2. Evaluation of Transplantation Rate of Organoids

In order to evaluate the transplantation rate according to the scaffold of the colon organoid transplanted in Example 1, it was carried out as follows.

On the 7th day after transplantation of colon organoids, the colon tissue was autopsied to measure GFP signals emitted from the transplanted organoids. Specifically, the organoid-implanted colon tissue was vertically incised to create a planar structure, and this tissue was spread thinly on a slide glass and a glass cover was covered thereon. At this time, the crypt was directed downward. The prepared slide glass was placed on the stage of a fluorescence microscope to observe the region where GFP fluorescence was expressed.

FIG. 1 is a photograph of measuring the GFP signal emitted from the organoid transplanted into the colon tissue on the 7th day after transplanting the colon organoid for each scaffold.

Figure 2:
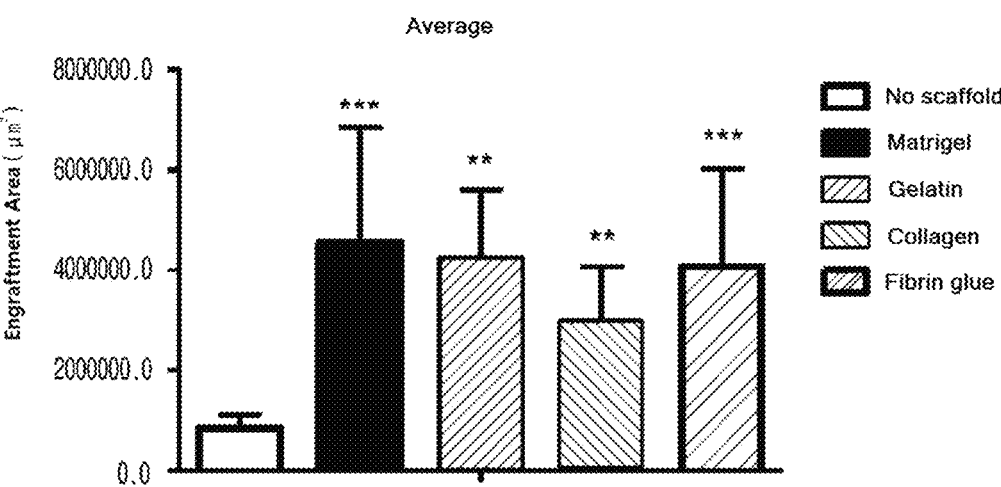
FIG. 2 is a graph showing the area of an organoid transplanted into the colon tissue on the 7th day after transplanting the colon organoid.

FIG. 2 is a graph showing the area of the organoid transplanted into the colon tissue on the 7th day after transplanting the colon organoid.

As shown in FIGS. 1 and 2, in the absence of a scaffold, it was confirmed that the GFP signal was the weakest and the transplantation rate was low. On the other hand, it was confirmed that when gelatin, collagen, and fibrin glue were used as scaffolds, the transplantation rate and transplanted area were similar to those when Matrigel, a positive control, was used as a scaffold. Therefore, when gelatin, collagen, or fibrin glue is used as a scaffold for organoid transplantation, the transplantation rate of organoids is significantly increased.

Example 3. Evaluation of Survival Rate and Engraftment Ratio of Organoids

In order to evaluate the survival rate and engraftment ratio according to the scaffold of the colon organoid transplanted in Example 1, it was carried out as follows.

10 to 13 animals were used for each scaffold experimental group, and tissue autopsy was performed one week after transplantation of GFP organoids into the colon. Those expressing GFP in the colon were classified as successfully transplanted animals, and those not expressing GFP were classified as unsuccessfully transplanted animals. The final engraftment ratio was determined by calculating the percentage of the number of successfully transplanted animals out of the total number. And the final survival rate was calculated by counting the animals who died within 7 days after transplantation.

The results are shown in Table 1 below.

TABLE 1

| | Number of trans- plantation | Engraft- ment successes | Engraft- ment failed | Dead rate (%) | Survival ratio (%) | Engraft- ment |
|---|---|---|---|---|---|---|
| No scaffold | 13 | 8 | 1 | 2 | 84.62 | 61.54 |
| Matrigel | 10 | 9 | 0 | 1 | 90.00 | 90.00 |
| Gelatin | 13 | 9 | 1 | 3 | 76.92 | 69.23 |
| Collagen | 10 | 9 | 1 | 0 | 100.00 | 90.00 |
| Fibrin glue | 10 | 9 | 0 | 1 | 90.00 | 90.00 |

Figure 3:
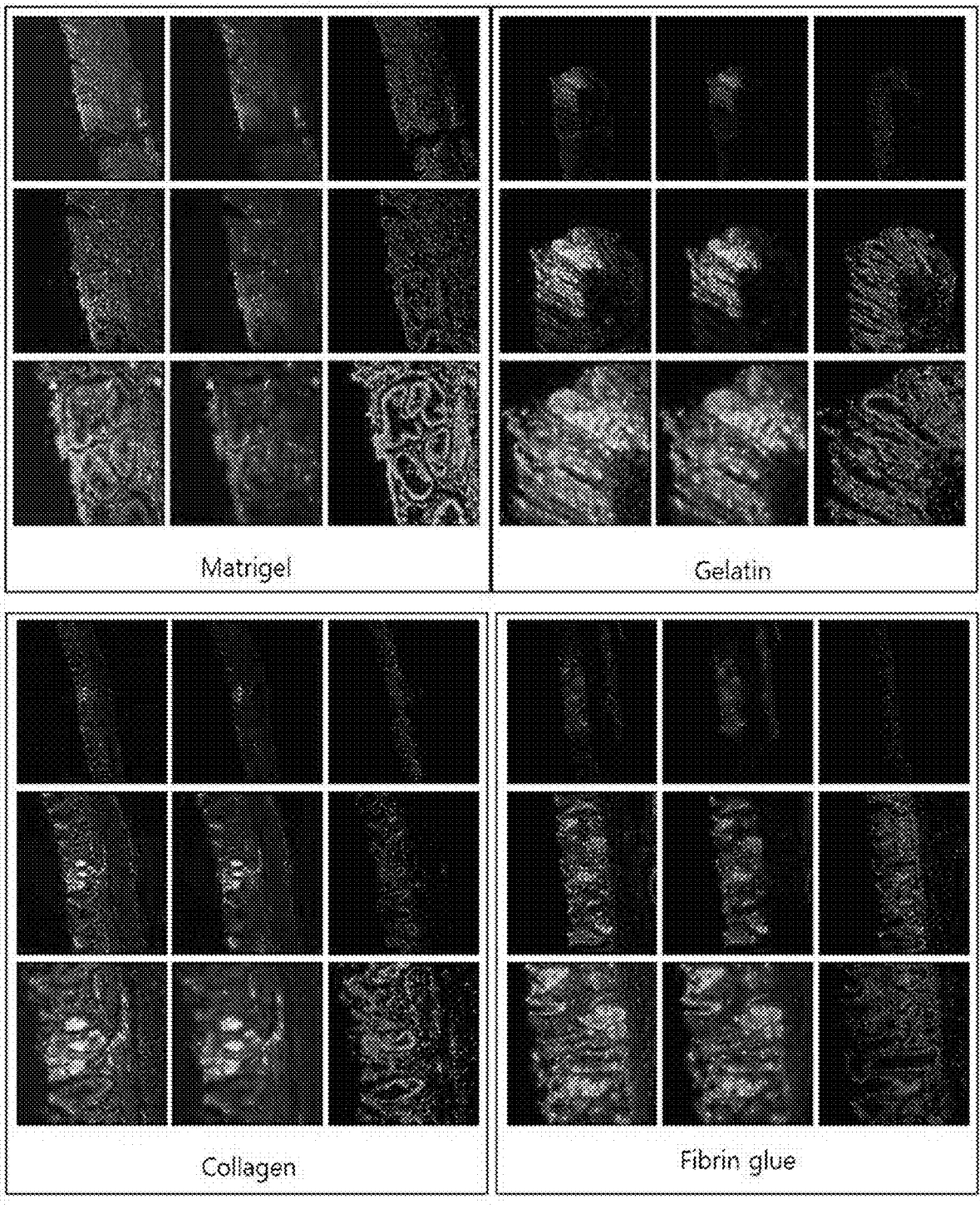
FIG. 3 is a photograph showing the result of observing a colon tissue section on the 7th day after transplanting colon organoids.

As shown in Table 1, when gelatin, collagen, and fibrin glue were used as scaffolds, the survival rates were 76.92, 100, and 90%, respectively, and the engraftment ratio was confirmed as high as 69.23, 90, and 90%, respectively. Therefore, it was confirmed that the survival rate and engraftment ratio were excellent. This was at a level similar to that in the case of using Matrigel, a positive control. FIG. 3 is a photograph showing the results of observing the colon tissue section on the 7th day after transplantation of colon organoids.

As shown in FIG. 3, when gelatin, collagen, and fibrin glue were used as scaffolds, it was confirmed that the organoids were successfully settled to form colonic crypts.

Example 4. Stability Evaluation

In order to evaluate the stability of the colon organoid transplanted in Example 1, an autopsy was performed on the 7th day after transplantation, and the morphology of the autopsied tissue and the occurrence of lesions were checked.

Figure 4:
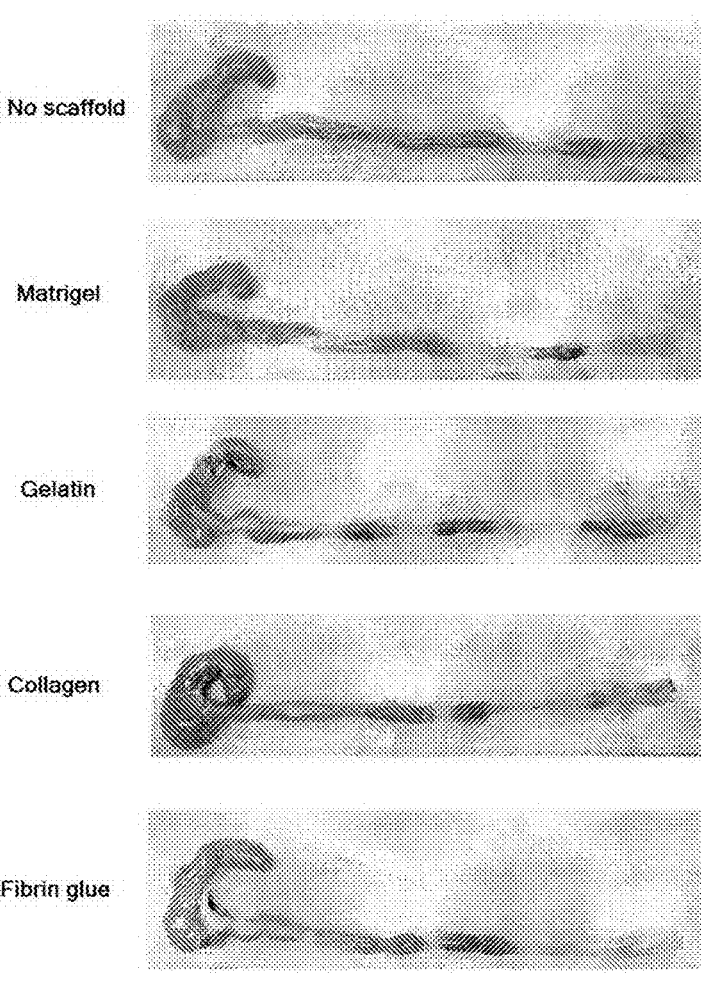
FIG. 4 is a photograph showing the morphology of a colon transplanted with an organoid on the 7th day after transplanting the colon organoid.

FIG. 4 is a photograph showing the morphology of the colon transplanted with the organoid on the 7th day after transplantation of the colon organoid.

As shown in FIG. 4, when gelatin, collagen, or fibrin glue was used as a scaffold, an edema or bloody stool that may appear in the colon transplanted with organoid was not observed in the autopsy tissue.

Figure 5:
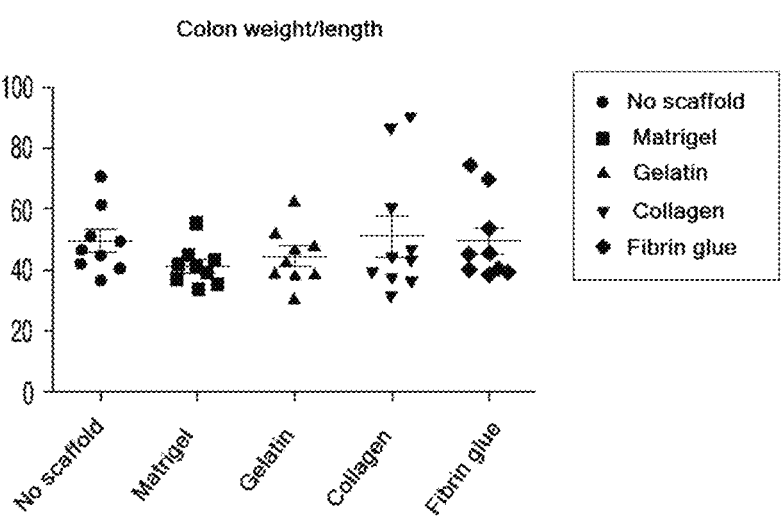
FIG. 5 is a graph showing the result of calculating the weight/length of a colon transplanted with an organoid on the 7th day after transplanting the colon organoid.

FIG. 5 is a graph showing the result of calculating the weight/length of the colon transplanted with the organoid on the 7th day after transplanting the colon organoid.

As shown in FIG. 5, the volume of edema that may appear when inflammation occurred was checked by calculating the weight/length of the colon transplanted with organoid. As a result, there was no significant difference compared with the control group using Matrigel.

Therefore, it was confirmed that when the organoid was transplanted using gelatin, collagen, or fibrin glue as a scaffold, the stability was excellent.

Example 5. Evaluation of Normal Organoid Formation from Transplanted Tissue

In order to evaluate whether normal organoids are formed from the transplanted colonic organoids in Example 1, a second colonic organoid (secondary organoid) was formed from the transplanted colonic tissue.

Specifically, after checking the GFP of the transplanted colon tissue with a fluorescence microscope, it was cut with surgical scissors, put in a tube containing crypt chelating buffer, and reacted in a shaking incubator at 37° C. for 20 minutes. And then, it was put in a 10 ml syringe equipped with an 18 gage needle, and crypt is separated by grinding 20 times. The separated crypt was centrifuged, collected, filtered through a 70 μm filter, mixed with Y-27632-added medium and matrigel at a 1:1 ratio, and inoculated at a concentration of 20 μl/well in a 48-well plate. After hardening the matrigel by putting it in an incubator at 37° C. for 30 minutes, a Y-27632-added medium was added and cultured for 5 days. On the 5th day of culture, colonic organoids expressing GFP were followed up.

Figure 6:
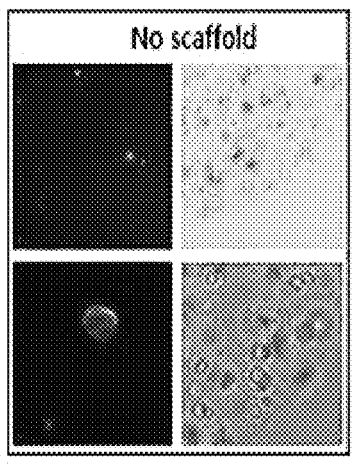
FIG. 6 is a photograph of the result of confirming the GFP signal after forming a secondary organoid after transplanting the colon organoid.
Figure 6:
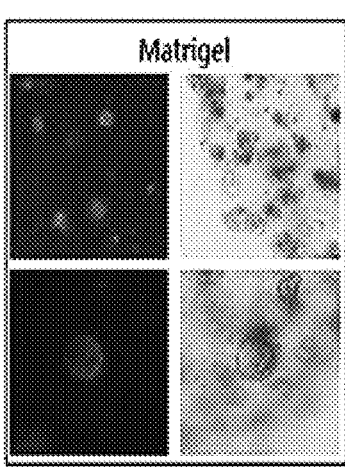
Figure 6:
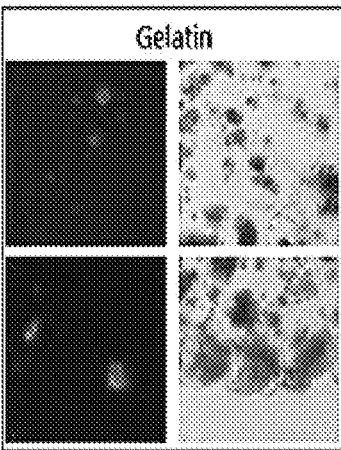
Figure 6:
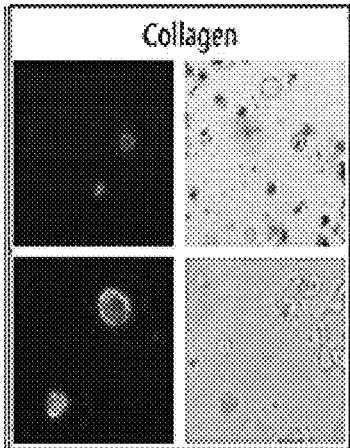
Figure 6:
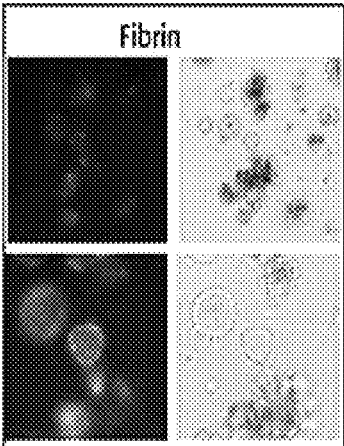

FIG. 6 is a photograph of the result of confirming the GFP signal after forming a secondary organoid after transplanting the colon organoid.

As shown in FIG. 6, when gelatin, collagen, or fibrin glue was used as a scaffold, secondary organoids expressing GFP were effectively formed. This was confirmed to be at a level similar to that of the positive control using matrigel.

Figure 7:
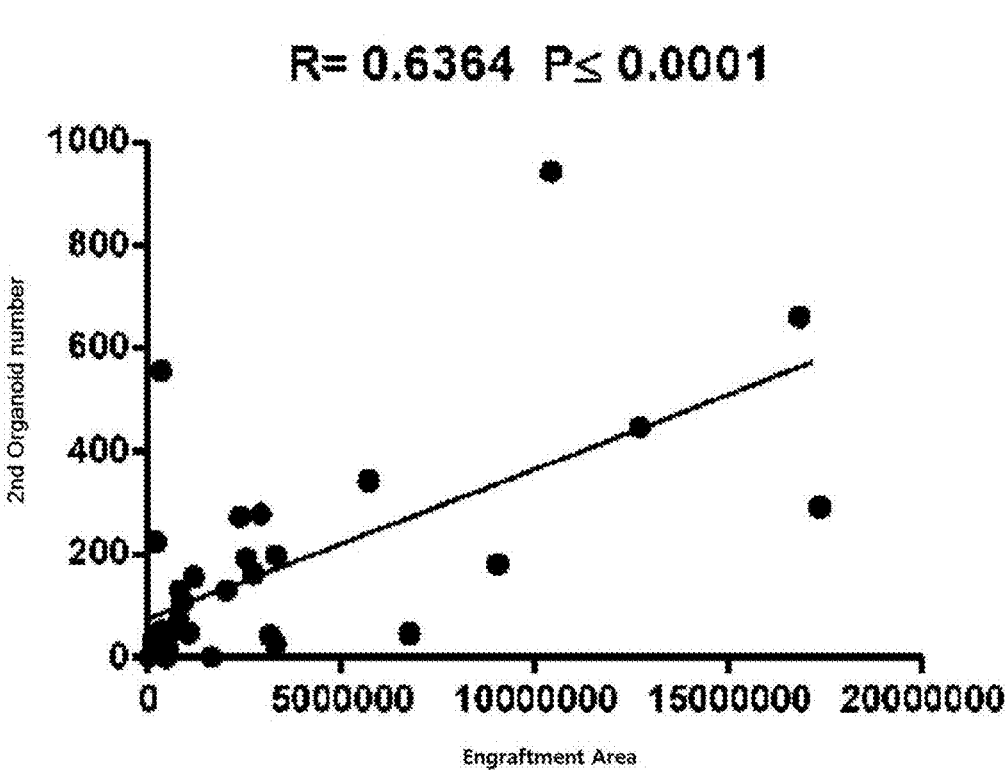
FIG. 7 is a graph showing the results of measuring a correlation with a transplanted area by measuring a number of GFP-expressing organoids after forming a secondary organoid after transplanting a colonic organoid.
Figure 8A:
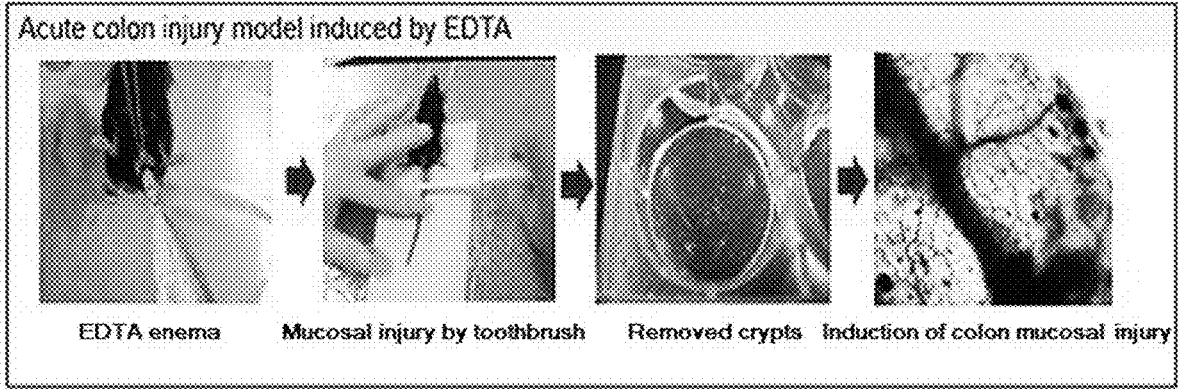
FIG. 8a is a schematic diagram showing the manufacturing process of the acute colon injury model induced by EDTA.
Figure 8B:
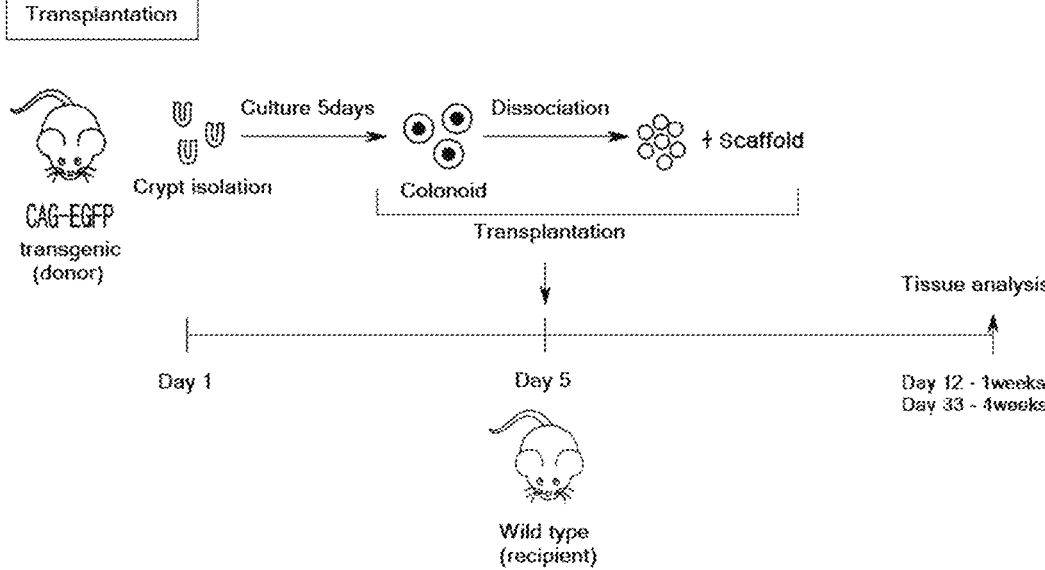
FIG. 8b is a schematic diagram illustrating a transplantation process of an organoid according to one embodiment.
Figure 8C:
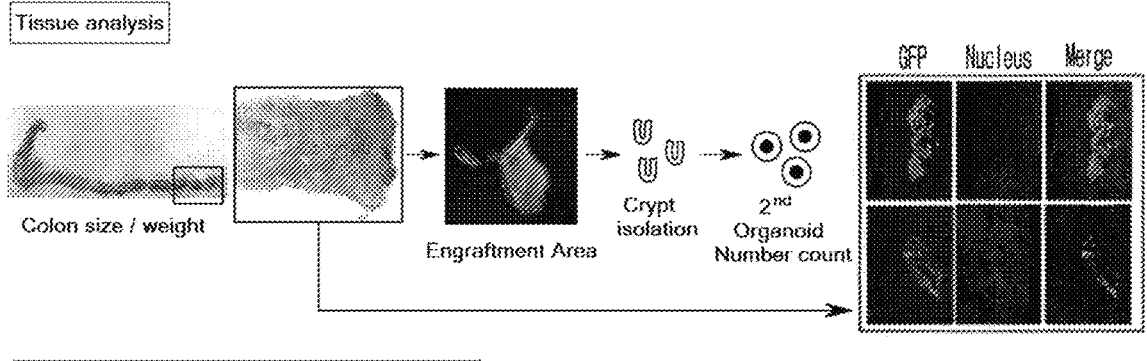
FIG. 8c is a result showing the tissue analysis result after transplantation of the organoid according to one embodiment.

FIG. 7 is a graph showing the results of measuring the correlation with the transplanted area by measuring the number of GFP-expressing organoids after forming a secondary organoid after transplanting colonic organoids.

As shown in FIG. 7, it was confirmed that the number and area of secondary organoids increased in proportion.

Therefore, it indicates that gelatin, collagen, and fibrin glue do not significantly affect normal organoid formation.

According to one aspect of the present invention, when collagen, gelatin, or fibrin glue is used as a scaffold for organoid transplantation, the transplantation rate and survival rate of the organoid is high and the stability is also excellent, therefore the composition comprising the same can be used usefully for biotransplantation in vivo.

What is claimed is:

1. A composition for biotransplantation consisting of organoid and fibrin glue, wherein the fibrin glue is comprised in an amount of 10 to 15% (v/v) based on the total weight of the composition.

2. The composition for biotransplantation according to claim 1, wherein the organoid is selected from the group consisting of intestinal organoid, retinal organoid, kidney organoid, liver organoid, gastric organoid, prostate organoid, breast organoid, inner ear organoid, cardiac muscle fiber organoid, hepatic endothelial organoid, pancreatic organoids, fallopian tube organoids, and cerebral organoids.

3. A method for transplanting an organoid, the method comprising mixing fibrin glue with the organoid to prepare the composition according to claim 1; and administering the composition to a subject.

* * * * *